United States Patent
Jasprova

(10) Patent No.: US 7,198,802 B2
(45) Date of Patent: Apr. 3, 2007

(54) TABLET OBTAINED BY DIRECT COMPRESSION COMPRISING 4-AMINO-1-HYDROXYBUTYLIDENE-1,1-BISPHOSPHONIC ACID AS ACTIVE INGREDIENT

(75) Inventor: Dagmar Jasprova, Prague (CZ)

(73) Assignee: Zentiva A.S., Prague (CZ)

( * ) Notice: Subject to any disclaimer, the term of this patent is extended or adjusted under 35 U.S.C. 154(b) by 529 days.

(21) Appl. No.: 10/257,958

(22) PCT Filed: Jun. 29, 2001

(86) PCT No.: PCT/CZ01/00037

§ 371 (c)(1), (2), (4) Date: Oct. 24, 2002

(87) PCT Pub. No.: WO02/03963

PCT Pub. Date: Jan. 17, 2002

(65) Prior Publication Data

US 2003/0161878 A1   Aug. 28, 2003

(30) Foreign Application Priority Data

Jul. 11, 2000 (CZ) .............................. PV20002567

(51) Int. Cl.
*A61K 9/20* (2006.01)

(52) U.S. Cl. ..................................................... 424/464
(58) Field of Classification Search ................. 424/464
See application file for complete search history.

(56) References Cited

U.S. PATENT DOCUMENTS

| 5,650,168 A | * | 7/1997 | Preis et al. ................... 424/465 |
| 5,853,759 A | * | 12/1998 | Katdare et al. .............. 424/466 |
| 6,455,572 B1 | * | 9/2002 | Day et al. ..................... 514/424 |

FOREIGN PATENT DOCUMENTS

| WO | 94 12200 | | 6/1994 |
| WO | WO 94 12200 | * | 6/1994 |
| WO | 98 42379 | | 10/1998 |

* cited by examiner

*Primary Examiner*—Michael P. Woodward
*Assistant Examiner*—Marc C. Fitzgerald
(74) *Attorney, Agent, or Firm*—Oblon, Spivak, McClelland, Maier & Neustadt, P.C.

(57) ABSTRACT

A tablet, obtainable by direct comprising the active ingredient 4-amino-1-hydroxybutylidene-1,1-bis-phosphonic (alendronic) acid or its pharmaceutically acceptable salts in an amount of 5 to 140 mg, based on the pure acid, a dry binder, a disintegrating agent, a lubricant, the tablet comprising, as the diluent, a combination of at least two diluents except lactose.

4 Claims, No Drawings

TABLET OBTAINED BY DIRECT COMPRESSION COMPRISING 4-AMINO-1-HYDROXYBUTYLIDENE-1,1-BISPHOSPHONIC ACID AS ACTIVE INGREDIENT

TECHNICAL FIELD

The invention applies to the pharmaceutical tablet formulations produced by the direct compression that contain 4-amino-1-hydroxybutylidene-1,1-bisphosphonic acid (hereinafter called "alendronic acid") and its pharmaceutically acceptable salts as the active ingredient that are of use in pharmaceutical practice and pharmaceutical excipients.

BACKGROUND ART

Effects of bisphosphonic acids on the skeletal system have been known for years. The inhibition of osteo-resorption due to an intake of the substances considered in rats has been published in Acta. Endocrinol. 76, 613 (1976) as well as the retardation of chronic arthritis progression in Brit. J. Pharmacology 21, 127 (1963). Patent literature describes the effect of 1-hydroxy-1,1-ethylidenebisphosphonic acid (U.S. Pat. No. 3,683,080/1972) and of 3-amino-1-hydroxy-1,1-propylidenebisphosphonic acid (DE Pat. 2 405 254/1974) on calcium metabolism, resp. The therapy of urolithiasis and osteo-resorption inhibition with 4-amino-1-hydroxy-1,1-butylidenebisphosphonic acid is described in U.S. Pat. No. 4,621,077 (1984).

Numerous patents also provide the information concerning the pharmaceutical formulations with the compounds above stated. For example, the composition of the pharmaceutical formulation consisting of 3-amino-1-hydroxy-1,1-propylidenebisphosphonic acid together with lactose, starch, and magnesium stearate for the tablet dosage form or together with lauryl sulphate for the capsule form is given in DE Pat. 24 05 524 (1974). The pharmaceutical formulation of bisphosphonic acids not specified particularly is registered by the patent EP 550 395 (1991) even if again lactose, starch, and stearic acid are shown as an example. The patent EP 274 158 (1986) claims for the rights on a family of bisphosphonates including heterocyclic substituent relating to the capsule (starch, lauryl sulphate) and tablet (lactose, starch, magnesium stearate) pharmaceutical forms. In the patent EP 600 834 (1992) covering the use of bisphosphonic acids that are already registered by the patent EP 550 392 above stated for fracture treatment the following pharmaceutical forms orally administered are specified: pellets with the core formed by the active ingredient and microcrystalline cellulose; tablets containing lactose, starch, gelatine, talc, magnesium stearate, and silicon dioxide.

The pharmaceutical dosage form specifically related to 4-amino-1-hydroxy-1,1-butylidenebisphonic acid (hereinafter "alendronic acid") and to its salts is described in Rosini's patent U.S. Pat. No. 4,621,077 (1984) including the examples of 10-mg and 20-mg formulations:

| Substance | mg | mg |
|---|---|---|
| Sodium alendronate | 25 | 12.5 |
| Lactose | 84 | 80 |
| Hydrolysed starch | 5 | 5 |
| Talc | 5 | 8.5 |
| Magnesium stearate | 1 | 1 |

The international patent application WO 95/29679 describes the process of manufacture of medicinal products containing alendronic acid salts based on the wet granulation. Such a process consists in mixing of the active ingredient and diluent to form a damp powder mass that is processed into granules by the wet granulation (e.g. in a planet granulator). The granules formed are dried, milled to a standard particle size, and blended with the disintegrating agent and the lubricant. After a final mixing the pre-compression mixture is compressed into the specified tablet form. Considering the composition given as the examples most tablets thus produced consist of lactose, microcrystalline cellulose, magnesium stearate, and of sodium salt of crosscarmellose. Apart from lactose the patent describes use of other diluents like calcium phosphate, mannitol, pulverised cellulose, pregelatinized starch, or microcrystalline cellulose. As a specifically preferred composition of diluents, a mixture of lactose and microcrystalline cellulose is mentioned. Lactose is known to be able to interact with sodium alendronate, especially in the presence of water, and to hasten its degradation. Microcrystalline cellulose is chemically inert towards alendronic acid, but it is somewhat hygroscopic, which again increases the amount of moisture and the possibility of interactions between lactose and the active ingredient. A granulation, let it be dry or wet, is an additional step of every technological process in comparison with direct compression. It makes possible to compress such mixtures that would not provide the requisite quality of the tablet in direct compression. On the other hand, especially wet granulation wherein the product is moistened and heated, forms unfavourable conditions for more sensitive organic substances.

Owing to its very appropriate compression characteristics lactose is undoubtedly a diluent of the widest use, but it still exhibits some objectionable properties. It browns frequently in the environment displaying high relative humidity (more than 80%). Moreover, this process accelerated by a heat is not reproducible with respect to the particular lactose kind (content of micro-impurities may be concerned). When the active ingredients including the primary amine group are applied, Maillard's reaction [L. C. Maillard: Compt.Rend. 154, 66 (1912)] accelerated by alkaline agents may take place and bring a medicinal product to get brown including a decrease of its active ingredient content. Therefore, lactose is not recommended to be applied to the preparation of medicinal products that contain primary amine groups, as it is the case of a majority of therapeutically efficient bisphosphonic acids.

An answer to the issue of bisphosphonic acids-lactose formulation seeks WO 94/12200 of the MSD Company. This patent application refers to the formulation and to the process of manufacture of medicinal products based on bisphosphonic acids using the direct compression process technology. As may be apparent from the document considered the tablet contains, in addition to the active ingredient, a diluent in the form of anhydrous or hydrated lactose, a dry binder, a disintegrating agent, and a lubricant. Characteristic features of the direct compression process described in the inventory above mentioned are, as follows:

Composition: active ingredient, anhydrous lactose, microcrystalline cellulose, magnesium stearate, and sodium salt of carmellose (carboxymethylcellulose).

Process of manufacture: The active ingredient is first blended with one-third of microcrystalline cellulose and with one-half of anhydrous lactose. The pre-mixture obtained is then blended with both remaining excipients and it is mixed again. Sodium salt of carmellose is added under mixing to be followed with magnesium stearate to finish the mixture blending. When homogenized the mixture is subjected to compression.

The described process avoids the rather lengthy and uneconomical manufacturing process involving granulation. As may be apparent from the results of comparative testing of the finished product stability performed at the temperature of 40° C. and relative humidity of 75% described in the patent application considered the process exhibiting a greater simplicity and economy provides the product of a higher stability. A sealed pack of the medicinal product produced by the direct compression still contains 98.5% of alendronate original quantity after three months as compared with 94.6% of alendronate in the granulated product. A lower product stability relating to the wet granulation is to be rectified by a drying agent; its presence in the granulated product has ensured alendronate content at the level of 99.7% after the stability testing.

The problem of product instability related to Maillard's reaction has not been quite solved by this measure either. A hygroscopic behaviour is encountered in the substances actually contained in the tablet (lactose, cellulose, carmellose; for details see Handbook of Pharmaceutical Excipients 1994, Editor: American Pharmaceutical Association, for example), and so, the medicinal product concerned sealed in common packs without desiccants absorbs atmospheric humidity progressively and its declared two-year stability under humid and warm storage conditions is very questionable on that account.

The patent application WO 99/04773, concerning the method of osteo-resorption inhibition based on once or twice a week dosage schedule, or, possibly, on one dose in a fortnight, claims also for the pharmaceutical compositions containing 70 mg or 140 mg of alendronic acid. The formulation actually described in the patent application considered fully corresponds to that of the patent application WO 94/12200, discussed above:

| Substance | mg |
|---|---|
| Sodium alendronate | 45.68 |
| Lactose | 71.32 |
| Microcrystalline cellulose | 80 |
| Crosscarmellose | 2 |
| Magnesium stearate | 1 |

It is evident from the review above given that the patent literature does not involve any excipient combination providing the full and adequate solution of the tablet formulation containing alendronic acid.

The theoretical approach to the discussed issue consists in a substitution of lactose with other diluents as may be, for example:

a) Mannitol

Mannitol is one of typical diluents applied to the preparation of tablets containing humidity-sensitive substances. Because it does not undergo Maillard's reaction (it does not include glycoside hydroxygroup) it suits the formulation with amines or amino acids, including aminobisphosphonic acids. Owing to its exclusive stability he serves as the additive in injection products containing aminobisphosphates.

The medicinal products containing lactose provided with a common package are not able to exhibit the adequate stability for a reasonable time period in highly humid surroundings of above 90-% relative humidity. Moreover, the products including amino acids are susceptible to Maillard's reaction under such humidity conditions. Instability of the products with mannitol due to excessive water content is obvious only at the relative humidity exceeding 98%.

Background experience relating to mannitol application in practice is quite well, especially as far as the wet granulation is concerned. However, mannitol use in case of the direct compression is not advisable due to its inferior compression characteristics.

b) Calcium Hydrogen Phosphate

Calcium hydrogen phosphate is another very stable diluent that fits to the mixtures processed by the direct compression. It possesses the desirable properties of high stability and compressibility but a certain alkalinity that may adversely affect the product stability belongs to its drawbacks.

c) Microcrystalline Cellulose

Microcrystalline cellulose (MCC) is to be used in the formulations prepared by the direct compression as the solid binder of a considerable effect on overall compression characteristics of a tablet. The increasing MCC content in a formulation results in lowering the requirements for the compressibility of a diluent. In some cases MCC is able to replace the diluent completely. MCC hygroscopicity may adversely affect the finished product stability.

d) Modified Starches

They provide another possibility as far as choice of the fillers of the formulations considered is concerned. Hygroscopicity of modified starches may adversely affect the finished product stability.

All the above cases concern agents that, unlike disaccharides of the lactose type, are not incompatible with aminophosphates of the type of alendronic acid. However, the degree of their stability and compression characteristics differ from case to case.

In experts' view the replacement of lactose with other diluent is less advisable. Such a position is to be explained by inferior compression properties of the substance concerned usually encountered. Diluents used in the formulation prepared by direct compression are often blamed for their inadequate compressibility that makes necessary the high-pressure compression machines to be applied to attain an appropriate hardness of the medicinal product. However, such a modification results in lower recovery of a tablet content and, consequently, in demand to use special and expensive disintegrating agents as sodium salt of carmellose above mentioned may be, for example. In some cases the direct compressed mixture may exhibit poor flow characteristics that may impair the adequate control on the tablet mass and, possibly, an efficient utilization of the fall capacity of sophisticated compression machines. A pre-compression mixture flow characteristics are often ameliorated by adding of stearates. Magnesium stearate is used for such a purpose most frequently.

The strong points of lactose as the diluent in formulations prepared by direct compression and apparent unsuitability of other diluents are best illustrated by their compression characteristics and equilibrium water content (adsorption isotherm) presented as the example.

A comparison of the compression characteristics of mannitol, cellulose, and of lactose is given e.g. in Handbook of Pharmaceutical Excipients Considering the compared substances mannitol granulate seems to be the most unsuitable for the direct compression because the increase of compression above 12 kN does not provide any increase in the tablet hardness dissimilar to lactose where the tablet hardness increases almost proportionally to the compression. This outcome is of a considerable importance in relation to a control of tablet quality. Compression characteristics of cellulose are practically identical with those of lactose over the whole range of compression values under examination.

A second significant parameter is a hygroscopicity of the substance considered.

Taking the hygroscopic properties of the compared substances into account mannitol seems to be the best diluent because its moisture starts to rise at about 98-% relative humidity. Lactose is very appropriate diluent even in relation to atmospheric humidity absorption because a significant increase in the water content is apparent above 90-% relative humidity of the air. Cellulose absorbs a relevant water quantity at 70-% atmospheric humidity already. The poor stability of the products containing the diluents examined is to be expected only in case of cellulose application, the best and very good one is related to mannitol and lactose use, resp.

These facts indicate that lactose integrates two characteristics of decisive importance for preparation of the tablets displaying a good quality and adequate stability. It is to be assumed accordingly that lactose replacement with other diluents is to bring about a deterioration of the product quality.

For example, mannitol is used when the relevant process of manufacture involving granulation does not rely on any particular parameters of the compression characteristics of excipients concerned as above shown. Microcrystalline cellulose, hydrogen phosphates, or starches enter the process as binders in smaller amounts and they are proposed to serve as diluents as well.

A deterioration of the product quality of a diverse extent for different active ingredients has to be taken into account in case of lactose replacement with another diluent. In general, it is not to be envisaged whether qualitative data relating to the product specified in a relevant pharmacopoeia will be met and the tablet will be ever used. It can be further assumed that where such quality is obtainable it will be necessary to find the specific composition in a relatively laborious optimization process.

The review of present state of the art in the field of techniques concerned indicates lactose, although entering into the chemical reaction with alendronate, to be an exceptionally suitable diluent integrating both an adequate stability (with the exception of very humid conditions where mannitol shows a higher stability) and good compressibility (similar to microcrystalline cellulose). Based on the adopted chart of compressibility and of adsorption isotherm it might be concluded that lactose replacement with other diluent will result in a tablet exhibiting either lower stability or inferior hardness.

Surprisingly, it has been found that lactose can be replaced with other diluent, a more stable product with all the assets of a high-grade tablet dosage form can be obtained, and thus the problem relating to Maillard's reaction with lactose can be solved accordingly.

The solution we propose provides a stable medicinal product in the tablet dosage form complying with all the requirements laid down on the orally administered medicines. In addition, these requirements are met over a wide range of concentrations of the excipients applied.

SUBSTANCE OF THE INVENTION

The invention includes a tablet, obtainable by direct compression, comprising the active ingredient 4-amino-1-hydroxybutylidene-1,1-bisphosphonic (alendronic) acid or its pharmaceutically acceptable salts in an amount of 5 to 140 mg, based on the pure acid, a diluent, a dry binder, a disintegrating agent, a lubricant, the tablet comprising, as the diluent, a combination of at least two diluents except lactose. As it has been found surprisingly, the use of such diluents makes the direct compression process to be applicable for the manufacture of alendronate tablets demonstrating appropriate physical properties and an adequate long-term stability.

Preferably, the tablet comprises at least two diluents except lactose, consisting of, based on the total weight of the tablet, 20 to 80% by weight of a diluent selected from microcrystalline or pulverised cellulose and calcium hydrogenphosphate and 0,001 to 50% by weight of one or more diluents selected from mannitol, modified starches and phosphates or hydrogenphosphates of alkali metals and alkaline earth metals.

The formulation considered meets the diverse requirements to be concerned, as follows:

a) it provides the product with a stability exceeding that of lactose formulations developed for the time being that is to be particularly apparent at higher active ingredient concentrations;

b) it makes possible to prepare small, smoothly-swallowable tablets when active ingredients of a lower potency are applied;

c) it maintains excellent both the compression characteristics of the pre-compression mixture and the finished tablet quality as displayed by the lactose formulation even in a wide range of diluent concentrations;

d) when applied, it provides the effect on osteo-resorption inhibition identical with that of the existing formulations. Accordingly, it can be administered for the treatment of diseases associated with bone tissue shedding as osteoporosis may be, in particular.

e) dissolution—release of the active substance into a liquid simulating gastric environment-, critical for bioavailability of the active substance, has better values than those specified in the standards. This factor, moreover, does not grow impaired in a humid environment with time.

In a preferred embodiment, the tablet of the invention comprises 20 to 75% by weight of a diluent selected from microcrystalline cellulose and calcium hydrogenphosphate, 5 to 50% by weight of a diluent selected from mannitol and calcium hydrogenphosphate and optionally up to 20% by weight of other diluents. A preferred composition of the diluent is 10 to 50% by weight of mannitol and 30 to 70% by weight of microcrystalline cellulose, based on the tablet weight.

As is documented below in the Examples, the combination of diluents according to the invention with exclusion of lactose makes it possible to obtain acceptable properties of the tablets in an economic compressing process, regardful of sensitive substances, which is free of any granulation or pre-granulation of the components. That brings about a new sight onto the bisphosphonic acids pharmacy as a whole.

A pharmaceutical formulation produced by direct compression usually includes dry binder, disintegrating agent, lubricant, and diluent.

Potential drawbacks relating to the diluent compressibility may be rectified by a suitable dry binder. The well-developed proportions of the diluent and the dry binder may improve even tablet disintegration in gastric juice medium and, consequently, the active ingredient availability for the human organism.

An application of unduly efficient disintegrating agent results in a considerable decrease of the tablet stability in humid surroundings. The same effect may be brought about by a choice of such a dry binder that contains a highly potent disintegrating component. Interactions of binding and disintegrating properties of the tablets are of a great importance with respect to optimization of the compression process. Disintegrating agents of a lesser activity that only supplement and support disintegration function of the dry binder are preferred as far as alendronic acid and its salts are concerned.

Lubricants are used in the formulations of the invention in a usual standard way.

Considering the combination of microcrystalline cellulose (MCC) and mannitol for example, MCC adopts the diluent function as well (in addition to the dry binder function) and a presence of another diluent, mannitol, may affect the formulation stability in a great extent.

Moreover, it has been found that the tablet of appropriate properties may be prepared based on use of the excipients other than the combination of cellulose and mannitol already detailed herein. For example, the combination of hydrogen phosphates with mannitol results in the product of a very high stability as well. Likewise a modified starch together with mannitol provides the medicinal product with an appropriate quality.

Even though a diluent combination or use of one excipient for several functions (e.g. MCC), resp., results in a product of more favourable characteristics, use of one only diluent in tablet formulation is applicable as well.

The optimization of tablet formulation is closely related to the intention to have the process of tablet manufacture as simple as possible and to avoid laborious operations that may unnecessarily extra burden a processed material with a heat or increased air humidity. The process of manufacture of the tablet containing 4-amino-1-hydroxybutylidene-1,1-bisphosphonic acid or its pharmaceutically acceptable salt in the amount of 5 to 140 mg based on the pure acid according to this invention is, as follows: a mixture comprising a (combination of) diluent(s), a disintegrating agent, and a dry binder is homogenized, after adding a lubricant followed by mixing the mixture is compressed into tablets. The issues relating to the compatibility of individual components contained in a mixture and to the mixture homogeneity are to be often answered when the direct compression is applied. Pre-compression mixture usually necessitates to be homogenized by step-by-step mixing of several smaller charges. A difficulty may be sometimes brought by very active disintegrating agents presented in the pre-compression mixture in low concentrations that may cause the product inhomogeneity due to even minor concentration differences. The formulation of optimal component proportions may simplify the process of pre-compression mixture preparation as a whole because two-step homogenization of such a mixture may be taken for sufficient to provide the mixture with specified characteristics.

Thr examples given below are intended to provide the details of a choice of the formulation displaying optimal component proportions and to demonstrate an appropriate stability of alendronate pharmaceutical form in accordance with this invention.

EXAMPLES

Example 1

Reference Test—Lactose (The Formulation Described in WO 94/12200)

The composition of one tablet (the values are given in mg):

| | |
|---|---|
| Sodium alendronate | 13.05 |
| Anhydrous lactose | 103.95 |
| Granulated microcrystalline cellulose | 80.00 |
| Sodium salt of carboxymethylcellulose | 2.00 |
| Magnesium stearate | 1.00 |

Process of manufacture: Alendronate is first blended with one-third of microcrystalline cellulose and with one-half of anhydrous lactose. The pre-mixture obtained is then blended with both remaining excipients and it is mixed again. Sodium salt of carmellose is added under mixing to be followed with magnesium stearate to finish the mixture blending. When homogenized by forth mixing the mixture is subjected to the compression.

Adopted Results of Stability Tests:

The data provided below relates to the active ingredient assay in the product in % referred to the initial state and to the product appearance (its colour has been examined for a compliance with white to almost white colour being the specification for this particular test).

Test conditions: 40° C., 75% R.H.

| Testing frequency | 3 months | 6 months |
|---|---|---|
| % referred to the initial state | 98.5 | — |
| Appearance | satisfactory | — |

Example 2

Optimization of the Formulation—a Chemically Inert Diluent

As compared with the known process of manufacture based on use of lactose (Example no. 1) lactose was replaced in the example considered with mannitol displaying a higher stability and carboxymethylcellulose was replaced with starch, exhibiting a lower activity and functioning as a dry binder at the same time instead of microcrystalline cellulose. Maize starch contained in the amount ten times lesser of mannitol is used as the tablet-disintegrating agent but not as the diluent.

Process of manufacture: A mixture of alendronate, mannitol, and maize starch is blended. Magnesium stearate is added to this pre-mixed mixture, afterwards. Following the additional mixing the mixture is subjected to the compression process.

| | |
|---|---|
| Sodium alendronate trihydrate | 13.05 |
| Maize starch | 11.15 |
| Mannitol | 104.50 |
| Magnesium stearate | 1.30 |

The described replacement of excipients has enabled to process the active ingredient amount identical with that given in Example no. 1, but into the tablet of smaller dimensions.

The formulation considered has provided the tablet with appropriate characteristics. The tablet physical properties are given in the table shown below in Example no.3.

Example 3

Optimalization of the Formulation Considered Under Example No.2.

Tablet Pharmaceutical Form—10 mg of Alendronic Acid (13.05 mg of Monosodium Alendronate Trihydrate)

Preliminary tests (illustrated in Example no.2) have indicated that the introduction of mannitol instead of lactose in the tablet containing 10 mg of alendronic acid assures the specified tablet parameters (time of disintegration less than 15 minutes, friability less than 1%) when the content of maize starch is about from 7 to 15%.

In order to attain very good and consistent characteristics of the pre-compression mixture the additional dry binder had to be used, however, as compared to Example no.2. The microcrystalline cellulose was chosen as the binder for this test set.

The development has been aimed to prepare such a formulation that will be capable to integrate strong points of both excipients and to suppress their drawbacks. Considering this particular case mannitol is to be taken for the bearer of product stability and the microcrystalline cellulose for an appropriate tablet hardness. The same process of manufacture has been used in all the examples given, as follows:

A mixture containing alendronate, mannitol, maize starch, and microcrystalline cellulose is blended in a container at the speed of stirrer of 14 r.p.m and under the normal temperature and humidity (25° C., 60% R.H.). Magnesium stearate is added to the pre-mixed mixture. After homogenization the pre-compression mixture is subjected to compression on a rotary compression machine to form the tablets of flat (cylindrical) or oval shape of 130 mg in the mass.

Preliminary control of the tablet quality has been made considering the following criteria.

The tablets have to meet the requirements specified in Ph.Eur. (Art. 97) or an in-house specification, if appropriate, as follows:

| Uniformity of mass: | ±5% |
|---|---|
| Disintegration: | in 15 minutes |
| Hardness: | NLT 30 N |
| Friability: | NMT 1%. |

Data on the composition given in all the tables below in mg always refer to one tablet.

A-formulation.

65% of mannitol (M) and 15% of microcrystalline cellulose (MCC)

| Sodium alendronate | 13.05 |
|---|---|
| Mannitol | 84.50 |
| Granulated microcrystalline cellulose | 20.00 |
| Maize starch | 11.15 |
| Magnesium stearate | 1.30 |

The tablet disintegration was completed in 1 minute (specification: NMT 15 min.) and hardness and friability values were well within limits of the specifications concerned. The formulation has been found to comply with the criteria adopted.

B-formulation.

30% of M and 50% of MCC

| Sodium alendronate | 13.05 |
|---|---|
| Mannitol | 42.00 |
| Granulated microcrystalline cellulose | 62.50 |
| Maize starch | 11.15 |
| Magnesium stearate | 1.30 |

The tablet friability has decreased even more and its transport properties have been found excellent. Accordingly, this formulation was chosen for additional tests.

C-formulation.

20% of M and 60% of MCC

| Sodium alendronate | 13.05 |
|---|---|
| Mannitol | 26.00 |
| Granulated microcrystalline cellulose | 78.50 |
| Maize starch | 11.15 |
| Magnesium stearate | 1.30 |

The tablet superb characteristics found in case of the former formulation have been kept.

D-formulation.

10% of M and 70% of MCC

| Sodium alendronate | 13.05 |
|---|---|
| Mannitol | 13.00 |
| Granulated microcrystalline cellulose | 91.50 |
| Maize starch | 11.15 |
| Magnesium stearate | 1.30 |

Physical parameters of all the tablet formulations shown above have met every specified requirement.

Comparison of the physical properties of alendronate tablets

| | | Example-formulation | | | | |
|---|---|---|---|---|---|---|
| | | 2 | 3A | 3B | 3C | 3D | 6 |
| Approximate content of microcrystalline cellulose (MCC) [%] | | 0 | 15 | 48 | 60 | 70 | 80 |
| Approximate content of mannitol (M) [%] | | 80 | 65 | 32 | 20 | 10 | 0 |
| | Requirement | | | | | | |
| Hardness [N] | NLT 25 N | 25 | 35 | 50 | 70 | 70 | 92 |
| Friability [%] | NMT 1% | 0.9 | 0.5 | 0.15 | 0.15 | 0 | 0 |
| Disintegration [s] | NMT 900 s | 90 | 50 | 20 | 15 | 15 | 15 |

It may be apparent from the data given above that the tablet containing mannitol as the diluent displays the physical properties complying with the specification. Increasing MCC portion results in a meaningful improvement of the properties considered. When MCC content approaches 50% an improvement of the examined properties raises abruptly (decrease of friability and of time of disintegration, and increase of hardness, resp.).

Example 4

The Formulation Displaying the Optimal Proportion of the Excipients Considered—Stability Tests.

Based on the tests briefly outlined in Example no.3 the formulation showing the characteristics that are in the best compliance with the requirements relating to compressibility and stability was chosen for follow-up stability tests performed on the tablets of the following composition.

One tablet contains (in mg):

| | |
|---|---|
| Sodium alendronate | 13.05 |
| Mannitol | 42.00 |
| Granulated microcrystalline cellulose | 62.50 |
| Maize starch | 11.15 |
| Magnesium stearate | 1.30 |

Process of the manufacture: A mixture containing alendronate, mannitol, maize starch, and granulated microcrystalline cellulose is blended. Magnesium stearate is added to the pre-mixed mixture, afterwards. After additional homogenization the pre-compression mixture is subjected to the compression applying the equipment and conditions, as mentioned in Example no.3.

Stability Tests

Four tablet batches have been prepared by the process described above. The results of their stability testing performed under the severest test conditions (40° C., 75% R.H.) are given below.

Individual Test Results

The values provided in the tables relate to the active ingredient assay in the product in % referred to the initial state and to the product appearance (its colour has been examined for a compliance with white to almost white one being the specification for this particular test), resp.

| a) A-batch | | |
|---|---|---|
| Testing frequency | 3 months | 6 months |
| % referred to the initial state (titration) | 99.4 | 100.1 |
| Appearance | satisfactory | satisfactory |

Tablet disintegration: it was fully completed in 1 minute (specification: in 15 min.).

Dissolution: 100% of the active ingredient was released in 30 minutes (specification: NLT 75% in 30 min.).

The tablet displays the properties considerably superior to those specified in the European Pharmacopoeia.

| Testing frequency | 3 months | 6 months |
|---|---|---|
| b) B-batch | | |
| % referred to the initial state (titration) | 100.7 | 99.7 |
| Appearance | satisfactory | satisfactory |

| Testing frequency | 3 months | 6 months |
|---|---|---|
| c) C-batch | | |
| % referred to the initial state (titration) | 100.3 | 100.7 |
| Appearance | satisfactory | satisfactory |
| d) D-batch | | |
| % referred to the initial state (titration) | 100.2 | 99.8 |
| Appearance | satisfactory | satisfactory |

Summary of the Mean Values Relating to Four Stability Tests

| Testing frequency | 3 months | 6 months |
|---|---|---|
| % referred to the initial state (titration) | 100.15 | 100.08 |
| Standard deviation | 0.47 | 0.39 |
| Standard deviation | 1.14 | 0.92 |

The obtained results demonstrate no decrease of the active ingredient quantity in the tablet considering 3-month and 6-month testing frequency at the accelerated tests of the tablet stability. The difference between two mean values is less than standard deviations concerned.

The mean value relating to all eight measurements amounting to 100.11±0.43% provides the evidence that the content of sodium salt of alendronic acid in the tablet after 3-and 6-month storage under the temperature of 40° C. and 75-% relative humidity approximates its initial 100-% value at the beginning of testing. None of the analyses performed has provided the resultant value less than 99% as far as the active ingredient content is concerned.

The findings above discussed demonstrate the stability of the formulation examined to be superior to that of the alendronate pharmaceutical form known for the time being (see Example no.1).

Example 5

Calcium hydrogen phosphate has been used as the diluent

Both examined formulations with calcium hydrogen phosphate were prepared by two-stage blending where the mixture of the active ingredient, calcium hydrogen phosphate, maize starch, and of mannitol or microcrystalline cellulose was homogenized first, magnesium stearate was then introduced to the mixture that was again homogenized by mixing and subjected to the compression, afterwards.

The tablet composition in the tables is given in mg per one tablet.

a) Formulation containing calcium hydrogen phosphate and microcrystalline cellulose

| | |
|---|---|
| Sodium alendronate | 13.05 |
| Calcium hydrogen phosphate | 42.00 |
| Granulated microcrystalline cellulose | 62.50 |
| Maize starch | 11.15 |
| Magnesium stearate | 1.30 | b) Formulation containing calcium hydrogen phosphate and mannitol

| | |
|---|---|
| Sodium alendronate | 13.05 |
| Mannitol | 42.00 |
| Calcium hydrogen phosphate | 62.50 |
| Maize starch | 11.15 |
| Magnesium stearate | 1.30 |

Both formulations have resulted in the tablets that have met the specifications relevant to tablet friability, hardness, and disintegration.

Example 6

Microcrystalline cellulose was used as the diluent

For the process of manufacture see Example no.3.

| | |
|---|---|
| Sodium alendronate trihydrate | 13.05 |
| Maize starch | 11.15 |
| Microcrystalline cellulose | 104.50 |
| Magnesium stearate | 1.30 |

The formulation examined has resulted in the tablets that have met the specifications relevant to tablet friability, hardness, and disintegration.

Example 7

Formulation containing 70 mg of alendronic acid.

For the formulation processing see Example no.3.

The tablet composition in the table is given in mg per one tablet.

| | |
|---|---|
| Sodium alendronate trihydrate | 91.35 |
| Maize starch | 10.00 |
| Microcrystalline cellulose | 97.50 |
| Mannitol | 48.65 |
| Magnesium stearate | 2.50 |

The time of disintegration of the tablets containing 70 mg of alendronic acid has been less than 1 minute (specification: NMT 15 minutes); the tablet friability has been found considerably less than specified 1%.

The invention claimed is:

1. A tablet, obtainable by direct compression, consisting of the active ingredient 4-amino-1-hydroxybutylidene-1,1-bisphosphonic acid or its pharmaceutically acceptable salts in an amount of 5 to 140 mg, based on the pure acid, diluent, a dry binder, a disintegrating agent, and a lubricant, wherein, based on the total weight of the tablet, the diluent consists of a combination of 20 to 80% by weight of a diluent selected from microcrystalline or pulverised cellulose and calcium hydrogenphosphate and 0,001 to 50% by weight of mannitol.

2. The tablet of claim 1, wherein the mannitol is present, based on the total weight of the tablet, from 10 to 50% by weight.

3. A process of manufacturing the tablet of claim 1, wherein a mixture of the active substance, the combination of diluents, the disintegrating agent and the dry binder is homogenized and, after adding the lubricant, compressed.

4. A process of manufacturing the tablet of claim 2, wherein a mixture of the active substance, the combination of diluents, the disintegrating agent and the dry binder is homogenized and, after adding the lubricant, compressed.

* * * * *